(12) United States Patent
Parsonage et al.

(10) Patent No.: US 9,999,410 B2
(45) Date of Patent: Jun. 19, 2018

(54) SYSTEMS AND METHODS FOR SEQUENTIAL MIXING OF ACTIVATOR IN BIOADHESIVE DELIVERY DEVICE

(71) Applicant: ST. JUDE MEDICAL PUERTO RICO LLC, Caguas, PR (US)

(72) Inventors: Edward E. Parsonage, St. Paul, MN (US); Zachary J. Tegels, Minneapolis, MN (US); Martha Escobar, Jordan, MN (US); Russell D. Terwey, St. Michael, MN (US); Troy T. White, Maple Grove, MN (US); Bernhard Kaeferlein, Champlin, MN (US); Timothy M. McGlinch, St. Paul, MN (US)

(73) Assignee: St. Jude Medical Puerto Rico LLC, Caguas, PR (US)

(*) Notice: Subject to any disclaimer, the term of this patent is extended or adjusted under 35 U.S.C. 154(b) by 220 days.

(21) Appl. No.: 13/770,714

(22) Filed: Feb. 19, 2013

(65) Prior Publication Data
US 2013/0253576 A1    Sep. 26, 2013

Related U.S. Application Data

(60) Provisional application No. 61/613,422, filed on Mar. 20, 2012.

(51) Int. Cl.
*A61B 17/08* (2006.01)
*A61D 1/00* (2006.01)
*A61B 17/00* (2006.01)

(52) U.S. Cl.
CPC .... *A61B 17/0057* (2013.01); *A61B 17/00491* (2013.01); *A61B 2017/0065* (2013.01);
(Continued)

(58) Field of Classification Search
CPC ...... A61B 17/0057; A61B 2017/00495; A61B 2017/0065; A61B 2017/00654; A61B 2017/00004; A61B 2017/00623; A61B 2017/00637; A61B 2017/00659; A61B 2017/22067; B65B 1/02
USPC ............. 604/15, 48, 57, 93.01, 103.04, 502; 606/108, 148, 190, 191, 194, 198, 200, 606/213, 214; 53/476
See application file for complete search history.

(56) References Cited

U.S. PATENT DOCUMENTS

| 4,979,942 A * | 12/1990 | Wolf ................ A61B 17/00491 222/137 |
| 6,620,125 B1 * | 9/2003 | Redl ................ A61B 17/00491 222/145.6 |

(Continued)

*Primary Examiner* — Elizabeth Houston
*Assistant Examiner* — Mohamed Gabr
(74) *Attorney, Agent, or Firm* — Dorsey & Whitney LLP

(57) ABSTRACT

A sealant delivery device includes a delivery tube, a bioadhesive container, and an adapter. The delivery tube includes proximal and distal ends. The bioadhesive container holds a sealant activator and a sealant precursor separated from each other. The adapter is interposed between the delivery tube and the bioadhesive container. The adapter includes a first channel member that couples a first lumen of the delivery tube to the sealant activator, and a second channel member that couples the first lumen to the sealant precursor. The adapter provides separation of the sealant activator and the sealant precursor until a position distal of the bioadhesive container.

13 Claims, 10 Drawing Sheets

(52) U.S. Cl.
CPC .............. *A61B 2017/00495* (2013.01); *A61B 2017/00659* (2013.01)

(56) References Cited

U.S. PATENT DOCUMENTS

| | | |
|---|---|---|
| 8,333,787 B2 | 12/2012 | Pipenhagen et al. |
| 8,506,592 B2 | 8/2013 | Killion et al. |
| 2001/0016709 A1* | 8/2001 | Tovey et al. ................... 604/153 |
| 2004/0267308 A1* | 12/2004 | Bagaoisan ......... A61B 17/0057 606/213 |
| 2005/0027240 A1* | 2/2005 | Fehr ....................... A61C 5/064 604/82 |
| 2008/0161757 A1* | 7/2008 | Nayak et al. .................... 604/82 |
| 2011/0166595 A1* | 7/2011 | Vidlund ............. A61B 17/0057 606/213 |
| 2011/0282383 A1 | 11/2011 | Vidlund et al. |
| 2013/0006299 A1 | 1/2013 | Pipenhagen et al. |
| 2013/0190808 A1 | 7/2013 | Tegels et al. |
| 2013/0190812 A1 | 7/2013 | Vidlund |
| 2013/0190813 A1 | 7/2013 | Tegels et al. |

* cited by examiner

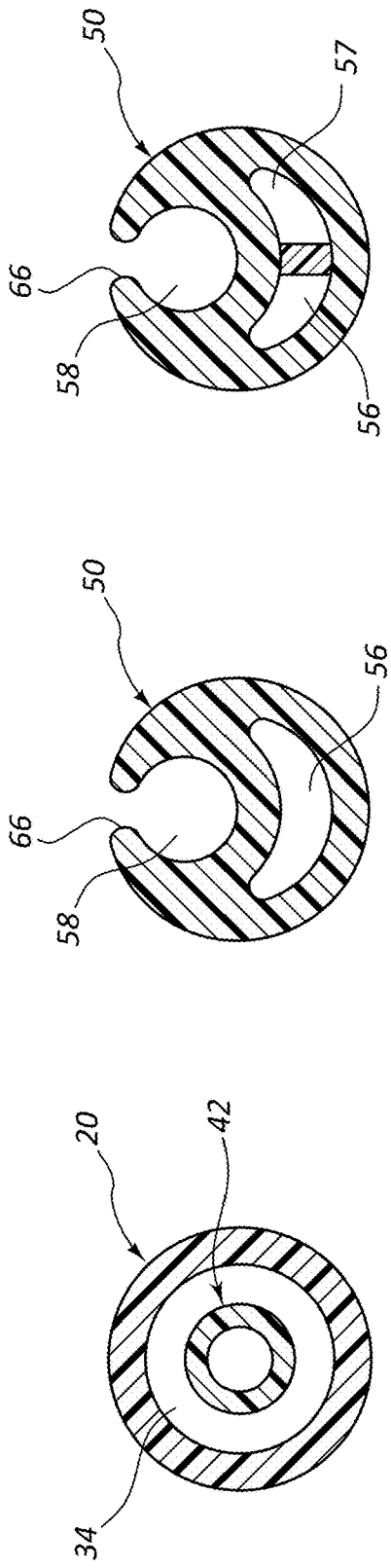
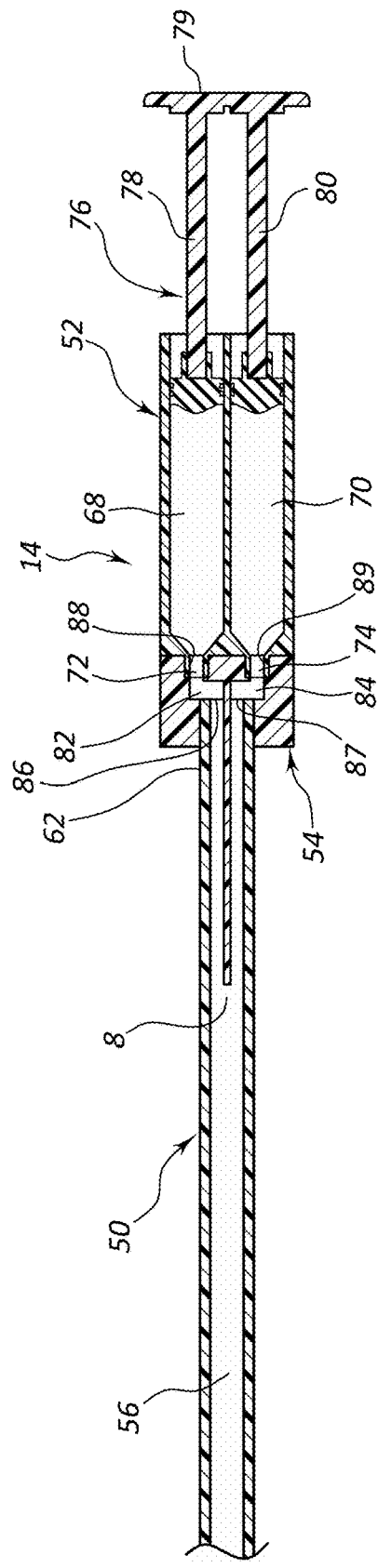
FIG. 1A  FIG. 1B  FIG. 1C  FIG. 1D

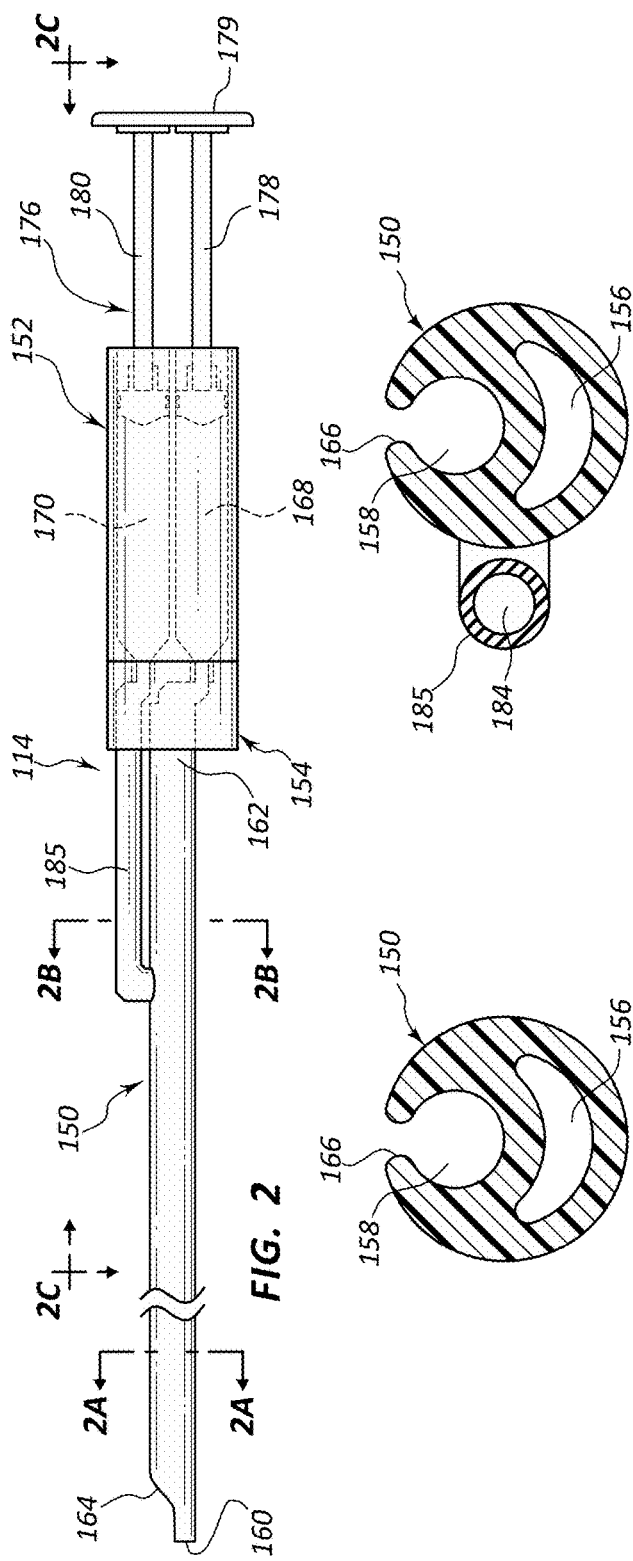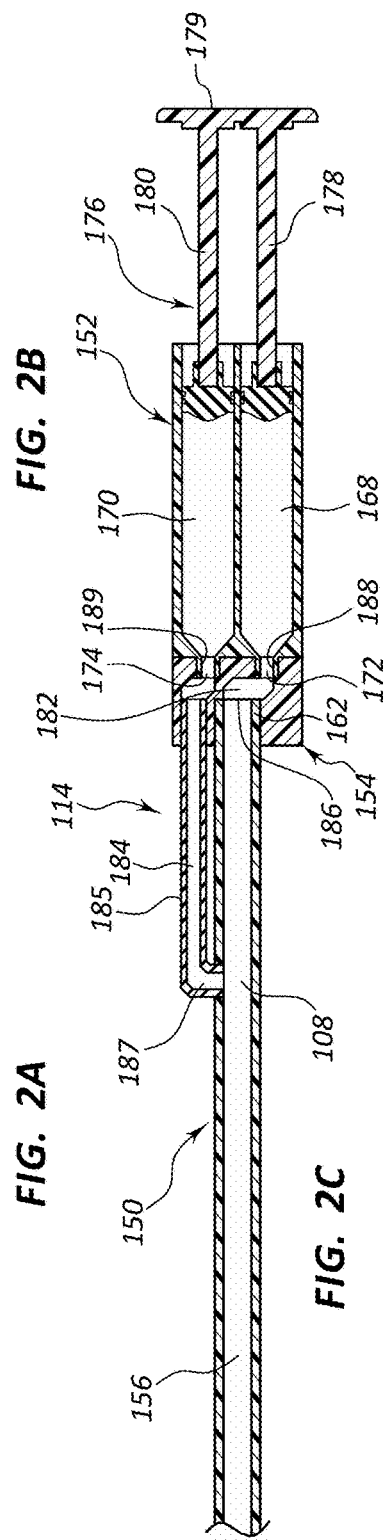

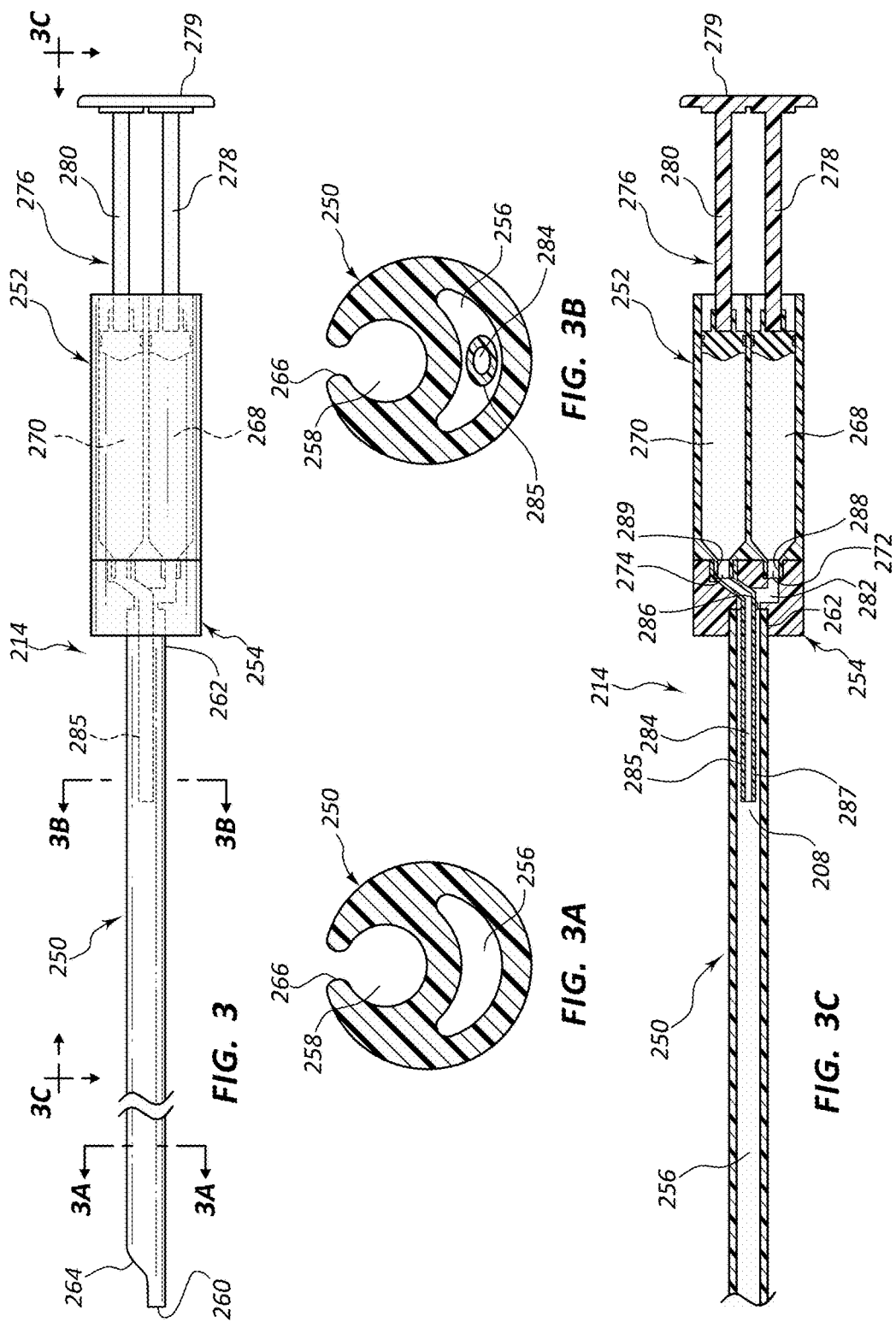

SYSTEMS AND METHODS FOR SEQUENTIAL MIXING OF ACTIVATOR IN BIOADHESIVE DELIVERY DEVICE

CROSS-REFERENCE TO RELATED APPLICATION

This application claims the benefit of the filing date of U.S. Provisional Application No. 61/613,422, filed 20 Mar. 2012, and entitled SYSTEMS AND METHODS FOR SEQUENTIAL MIXING OF ACTIVATOR IN BIOADHESIVE DELIVERY DEVICE, the disclosure of which is incorporated, in its entirety, by this reference.

TECHNICAL FIELD

The present disclosure relates generally to methods and systems for sealing tissue punctures, and more particularly, to methods and systems for handling and mixing of components of a bioadhesive sealant during delivery of the bioadhesive sealant to a tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one primary problem is insuring a complete seal of the puncture. One technique includes the use of a bioadhesive material to seal the puncture. Some types of bioadhesive materials must be activated prior to use, and should be activated just prior to use in order to avoid premature activation of the bioadhesive material. The handling and activation of bioadhesive materials for use in vascular and other tissue puncture closure applications present a number of challenges, particularly when using bioadhesive sealant components that have a quick set time.

SUMMARY

One aspect of the present disclosure relates to a bioadhesive delivery system that includes a delivery tube, a bioadhesive container, and a channel arrangement. The delivery tube includes proximal and distal ends and a delivery lumen. The bioadhesive container includes first and second chambers holding first and second sealant components, respectively. The channel arrangement includes a first channel member providing flow communication between the first chamber and the delivery lumen, and a second channel providing flow communication between the second chamber and the delivery lumen distal of the proximal end. The channel arrangement is configured to isolate the first and second sealant components from each other until the first and second sealant components are positioned within the delivery tube.

The first channel may be connected in flow communication with the delivery lumen at an open proximal end of the delivery tube. The second channel may be connected in flow communication with the delivery lumen through a side wall of the delivery tube. The second channel may extend into the delivery lumen at an open proximal end of the delivery tube. At least one of the first and second channels may comprise a length of tube. The bioadhesive container may be detachable from the delivery tube. At least a portion of the channel arrangement may be permanently mounted to the delivery tube. The channel arrangement may be interposed between the bioadhesive container and the delivery tube. The first sealant component may include a precursor mixture and the second sealant component may include an activator.

Another aspect of the present disclosure relates to a sealant delivery device that includes a delivery tube, a bioadhesive container, and an adapter. The delivery tube includes proximal and distal ends. The bioadhesive container holds a sealant activator and a sealant precursor separated from each other. The adapter is interposed between the delivery tube and the bioadhesive container. The adapter includes a first channel member that couples the delivery tube to the sealant activator, and a second channel member that couples the delivery tube to the sealant precursor. The adapter provides separation of the sealant activator and the sealant precursor until the sealant activator and sealant precursor reach the delivery tube.

The adapter may include a tube defining the second channel and extending distal of a proximal end of the delivery tube. The delivery tube may include first and second lumens arranged in parallel, wherein the first and second lumens are connected in flow communication with the first and second channels, respectively, and the first and second lumens intersect at a position distal of a proximal end of the delivery tube. The delivery tube may be detachable from the bioadhesive container to replace the delivery tube and provide multiple uses for the bioadhesive container. The first sealant component may include a precursor mixture and the second sealant component may include an activator.

Another aspect of the present disclosure relates to a method of delivering bioadhesive sealant to a tissue puncture. The method includes providing a delivery tube and a bioadhesive container, wherein the delivery tube includes a delivery lumen and proximal and distal ends, and the bioadhesive container includes at least first and second chambers holding first and second sealant components, respectively. The method also includes connecting the bioadhesive container to the proximal end of the delivery tube, and advancing the first and second sealant components into the delivery lumen while maintaining separation of the first and second sealant components until a location distal of the bioadhesive container and the proximal end of the delivery tube.

At least one of the bioadhesive container and delivery tube may include multiple channels that maintain separation of the first and second sealant components to a location distal of the bioadhesive container and the proximal end of the delivery tube. The method may include providing an adapter configured to maintain separation of the first and second sealant components until a location distal of the bioadhesive container and the proximal end of the delivery, tube. The method may include mixing the first and second sealant components within a lumen of the delivery tube, and delivering the mixed first and second sealant components to a distal end of the delivery tube where the mixed first and second sealant components are ejected from the delivery tube at a tissue puncture as a first sealant volume. The method may include adjusting a position of the delivery tube relative to the tissue puncture and ejecting the first and second sealant components from the delivery tube as a second sealant volume. The method may include detaching the delivery tube from the bioadhesive container and connecting the bioadhesive container to a different delivery tube for delivery of a second sealant volume of the mixed first and second sealant components at the tissue puncture.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1A is cross-sectional view of a balloon inflation device of the vascular closure system of FIG. 1 taken along cross-section indicators 1A-1A.

FIG. 1B is a cross-sectional view of a sealant delivery device of the vascular closure system of FIG. 1 taken along cross-section indicators 1B-1B.

FIG. 1C is a cross-sectional view of the balloon inflation device of FIG. 1 taken along cross-section indicators 1C-1C.

FIG. 1D is a cross-sectional view of the balloon inflation device of FIG. 1 taken along cross-section indicators 1D-1D.

FIG. 2 is a side view of another example balloon inflation device in accordance with the present disclosure.

FIG. 2A is a cross-sectional view of the balloon inflation device of FIG. 2 taken along cross-section indicators 2A-2A.

FIG. 2B is a cross-sectional view of the balloon inflation device of FIG. 2 taken along cross-section indicators 2B-2B.

FIG. 2C is a cross-sectional view of the balloon inflation device of FIG. 2 taken along cross-section indicators 2C-2C.

FIG. 3 is a side view of another example balloon inflation device in accordance with the present disclosure.

FIG. 3A is a cross-sectional view of the balloon inflation device of FIG. 3 taken along cross-section indicators 3A-3A.

FIG. 3B is a cross-sectional view of the balloon inflation device of FIG. 3A taken along cross-section indicators 3B-3B.

FIG. 3C is a cross-sectional view of the balloon inflation device of FIG. 3 taken along cross section indicators 3C-3C.

Throughout the drawings, identical reference numbers designate similar, but not necessarily identical, elements.

DETAILED DESCRIPTION

Figure 1:
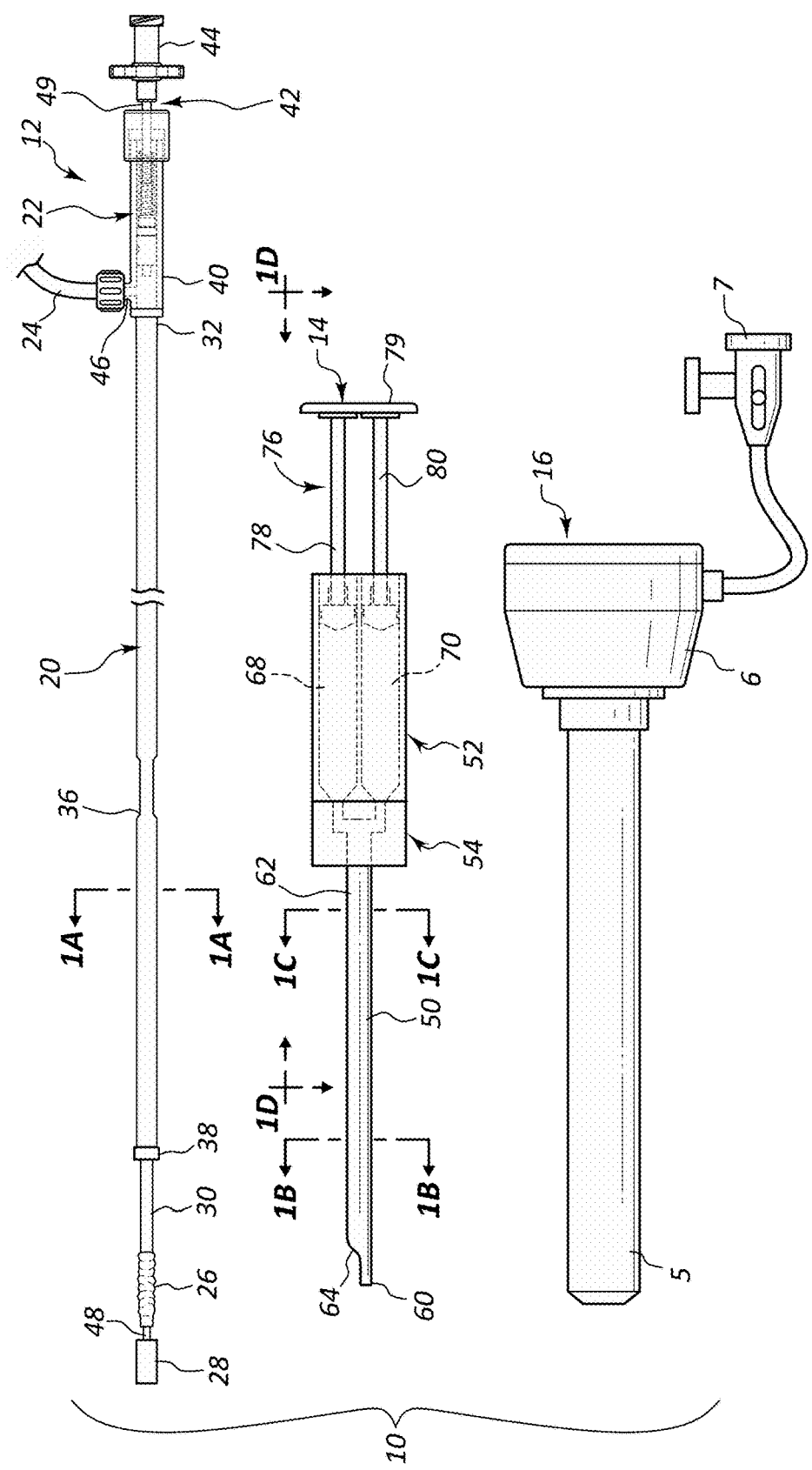
FIG. 1 is a side view of an example vascular closure system in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising.".

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure includes a vascular closure system used to seal a puncture in a vessel. The vascular closure system includes a balloon inflation device, a sealant delivery device, and a sheath. The sheath is used to gain access to the vessel puncture through a tissue tract. The balloon inflation device provides an anchor within the vessel to temporarily seal the vessel puncture from within the vessel. The temporary seal may be maintained while delivering a sealant to the vessel puncture using the sealant delivery device. In some embodiments, the sealant delivery device is integrated into the balloon inflation device as a single assembly. In other embodiments, the sealant delivery device is provided as a separate device that is connected to and disconnected from the balloon inflation device during a sealant procedure.

The sealant delivery device typically is configured to hold a plurality of sealant components separated from each other until just prior to mixing and delivering the sealant components to the vessel puncture. One aspect of the present disclosure provides for separation of the sealant components within the sealant delivery device until the sealant components are positioned within a delivery tube of the sealant delivery device. The delivery tube is typically positioned distal of a sealant container having a plurality of sealant chambers that hold the plurality of sealant components separated from each other.

The sealant delivery device may include an adaptor or connector interposed between the delivery tube and sealant container that helps maintain separation of the sealant components and route the sealant components from the sealant container to at least one sealant lumen of the delivery tube.

One aspect of the present disclosure relates to a method and system for handling short set time bioadhesive sealant components for use in an extra-vascular closure application. The system may include use of a bioadhesive delivery catheter having separate lumens for each of the sealant components of the bioadhesive sealant. The sealant components may comprise a precursor mixture and an activator. The activator may be mixed at a location distal of a location where the precursor and activator exit the sealant container (e.g., a distal tip of a dual chamber syringe). By providing mixing of the sealant components at a location distal of the exit point of the sealant container, the risk of clogging at the exit of the sealant container is minimized thereby providing an opportunity for reuse of the sealant container or other portions of the sealant delivery device.

In one example, a dual chamber syringe that carries a mixed precursor in one chamber and a curing activator in the other chamber is used as part of a sealant delivery device that provides multiple injections of bioadhesive sealant at different stages of sealing a vessel puncture. Providing mixing of the precursor and activator at a location spaced distal of the ejection ports of the dual chamber syringe avoids clogging of the syringe orifices that may otherwise occur due to backflow of the mixed precursor and activator components, and may otherwise preclude a second ejection from the dual chamber syringe. The activator may be mixed with the precursor at a location in the sealant delivery device that is downstream of the syringe orifices, thus eliminating the problem of syringe clogging and providing for multiple uses of the syringe to deliver a short set time bioadhesive sealant to a vessel puncture. The downstream location may be within the delivery tube. Alternatively, the downstream location may be within an adaptor or connector that is interposed between the delivery tube and syringe (e.g., sealant container).

Referring now to FIGS. 1-1D, an example vascular closure system 10 includes a balloon inflation device 12, a sealant delivery device 14, and a sheath 16. The sheath may be used to gain access to a vessel interior via a tissue tract and vessel puncture. The balloon inflation device 12 may be routed through the sheath to position an inflatable balloon within the vessel. The inflatable balloon of the balloon inflation device may be inflated and positioned against an inner surface of the vessel adjacent to the vessel puncture to temporarily seal the vessel puncture while a sealant is delivered to the vessel puncture by the sealant delivery device. The sealant delivery device may be advanced along the balloon inflation device to the vessel puncture. In at least some arrangements, the sheath is withdrawn prior to advancing the sealant delivery device to the vessel puncture.

The sealant delivery device may be configured to deliver a flowable sealant in multiple stages of sealing the vessel puncture. For example, a first volume of sealant may be deposited at the vessel puncture using the sealant delivery device while the balloon of the balloon inflation device is temporarily sealing the vessel puncture from within the vessel. In a secondary sealing step, the balloon is deflated and removed from the vessel puncture, and the sealant delivery device operates to deliver a second volume of sealant to further seal the vessel puncture and tissue tract leading to the vessel puncture (e.g., fill a channel or void left in the first volume of sealant upon removable of the balloon inflation device).

The balloon inflation device 12 may include an inflation tube 20, a balloon location device 22, an inflation source 24, a balloon 26, and a detachable tip 28. The inflation tube 20 may include distal and proximal ends 30, 32, an inflation lumen 34, an exchange port 36, and a positioning collar 38. A balloon 26 is positioned at the distal end 30. Inflation fluid is delivered through the inflation lumen 34 to inflate balloon 26 (see FIG. 1A). The exchange port 36 may be used to mount the sealant delivery device 14 to the balloon inflation device 12 as will be described in further detail below. The collar 38 may be used as a distal position stop for the sealant delivery device 14 as it is advanced along the inflation tube 20 to a position adjacent to the vessel puncture.

The balloon location device 22 may include a housing 40, an inner tube 42, an inner tube manifold 44, and an inflation port 46. The inner tube 42 may include distal and proximal ends 48, 49. The detachable tip 28 may be mounted at the distal end 48. The inner tube manifold 44 may be positioned at the proximal end 49. The balloon location device 22 may be used to provide a visual indication to an operator of at least one of a pressure condition, size, shape or other characteristic of the balloon 26. Details concerning operation of the balloon location device 22 and other possible features of balloon inflation device 12 are shown and described in U.S. Patent Application No. 61/590,000 filed on 24 Jan. 2012 and entitled "Balloon Location Device Manifold for Vascular Closure Device and Methods," which is incorporated herein in its entirety by this reference.

The sealant delivery device 14 includes a delivery tube 50, a sealant container 52, and an adaptor or connector 54. The sealant delivery device 14 is shown in FIG. 1 as a device separate from a balloon inflation device 12. Other configurations are possible wherein features of the sealant delivery device 14 are integrated into balloon inflation device 12.

The delivery tube 50 includes a sealant lumen 56, a secondary sealant lumen 57, and an exchange lumen 58 (see FIGS. 1B-1D). The sealant lumen 56 includes distal and proximal ends 60, 62. A secondary sealant lumen 57 includes a distal opening 64. The sealant lumen 56 includes a side opening 66. The sealant lumen 56 may define or provide a mixing zone or area 8 within which sealant components carried by the sealant container 52 are mixed as they are delivered to the distal end 60 prior to being ejected at the vessel puncture. Typically, at least some mixing of the sealant component is desired prior to the sealant components be ejected at the vessel puncture. Once the sealant components are mixed, the sealant material begins to set into a solid or semi-solid state. The mixed sealant material within the sealant delivery device 14 may clog ports or obstruct passages needed for future delivery and mixing of the sealant components as part of a secondary ejection at the vessel puncture. There may be advantages to positioning the mixing area or zone 8 within the sealant delivery device or location spaced as close to the distal end of the delivery tube 50 as possible to avoid clogging problems as the sealant material cures or sets. However, the need for adequate mixing of the sealant components prior to ejection at the vessel puncture may make it advantageous to position the mixing area or zone 8 as far from the distal end 60 of the delivery tube 50 as possible. Thus, as shown in FIG. 1B, the sealant lumen 56 and secondary sealant lumen 57 may comprise different cross-sectional shapes relative to each other. Similarly, lumens 156, 158 in FIG. 2B may comprise different cross-sectional shapes relative to each other, and lumens 256, 284 in FIG. 3B may also comprise different cross-sectional shapes relative to each other.

The sealant container 52 may include first and second sealant chambers 68, 70, first and second delivery tips 72, 74, and a plunger 76. Plunger 76 may include first and second plunger members 78, 80 and an actuator 79 used to advance the plunger 76. Each of the first and second sealant chambers 68, 70 carry components of a bioadhesive sealant. For example, the first sealant chamber 68 may carry a mixed precursor, and the second sealant chamber 70 carries an activator component. Other types of sealant components may be carried in the sealant container 52. The sealant container 52 may include three or more sealant chambers carrying various sealant components.

The adaptor 54 may include first and second sealant channels 82, 84. The adaptor 54 may be referred to as a channel member or channel arrangement. The first sealant channel 82 includes a first distal end 86 and a first port 88. The second sealant channel 84 includes a second distal end 87 and a second port 89. The first and second sealant channels 82, 84 provide flow communication between the first and second sealant chambers 68, 70 and the sealant lumen 56 of the delivery tube 50. The first and second delivery tips 72, 74 are mounted to the first and second ports 88, 89 (see FIG. 1D). The first sealant channel 82 is connected in flow communication with the sealant lumen 56 at the proximal end 62. The second sealant channel 84 is connected in flow communication with the secondary sealant lumen 57 provided in the delivery tube 50.

The arrangement of the delivery tube 50 and adaptor 54 provide isolation of the sealant components carried by the first and second sealant chambers 68, 70 until the sealant components are advanced distally from the first and second delivery tips 72, 74. The delivery tube 50 provides a mixing area or zone 8 within sealant lumen 56 at a location adjacent to distal opening 64 of the secondary sealant lumen 57. The mixing zone 8 for the sealant components may be positioned distal of a proximal end 62 of the delivery tube 50. Any backflow of the mixed first and second sealant components that have been mixed within the sealant lumen 56 typically does not advance proximately a distance sufficient to clog either of the first and second delivery tips 72, 74 or even the first and second sealant channels 82, 84. Other embodiments of a sealant delivery device are possible to provide isolation of the sealant components until a location distal of at least one of the sealant container 52 (e.g., the first and second delivery tips 72, 74), the adaptor 54, or a proximal end 62 of the delivery tube 50.

Referring now to FIGS. 2-2C, another example sealant delivery device 114 includes a delivery tube 150, a sealant container 152, and an adaptor 154. The sealant delivery device 114 includes a channel or tube positioned exterior of the delivery tube 150 to advance or delivery at least one of the sealant components in isolation until it reaches a location distal of the sealant container 52 (i.e., a location spaced distal of a proximal end of the delivery tube 150), Delivery tube 150 includes a sealant lumen 156, and an exchange lumen 158 (see FIG. 2A). The sealant lumen 156 includes distal and proximal ends 160, 162. The exchange lumen 158 includes a side opening 166 and a distal opening 164.

The sealant container 152 includes first and second sealant chambers 168, 170, first and second delivery tips 172, 174, and a plunger 176. The plunger 176 includes first and second plunger members 178, 180 and an actuator 179. The adaptor 154 includes first and second sealant channels 182, 184. The first sealant channel 182 includes a first distal end 186 and a first port 188. The second sealant channel 184 includes a second distal end 187 and a second port 189. The second sealant channel 184 is defined at least in part by a tube 185 that extends along an exterior of the delivery tube 150. The second sealant channel 184 extends from the second delivery tip 174 of the second sealant chamber 170 to a location spaced distal of the sealant container 152 and a proximal end 162 of the delivery tube 150. A mixing zone 108 is positioned within the sealant lumen 156 where the second sealant channel 184 intersects and is in flow communication with the sealant lumen 156.

The first sealant channel 182 provides flow communication between the first delivery tip 172 of the first sealant chamber 168 and the sealant lumen 156 at the proximal end 162 and delivery tube 150 (see FIG. 2C). Providing the mixing zone 108 at a location spaced distal of the first and second delivery tips 172, 174 and distal of the proximal end 162 of the delivery tube 150 reduces the likelihood of clogging of the first and second delivery tips 172, 174 due to the quick set characteristics of the combined sealant components which might otherwise limit the ability to make multiple deposits of sealant material at the tissue puncture using a single sealant delivery device 114 or single sealant container 152.

Figure 3D:
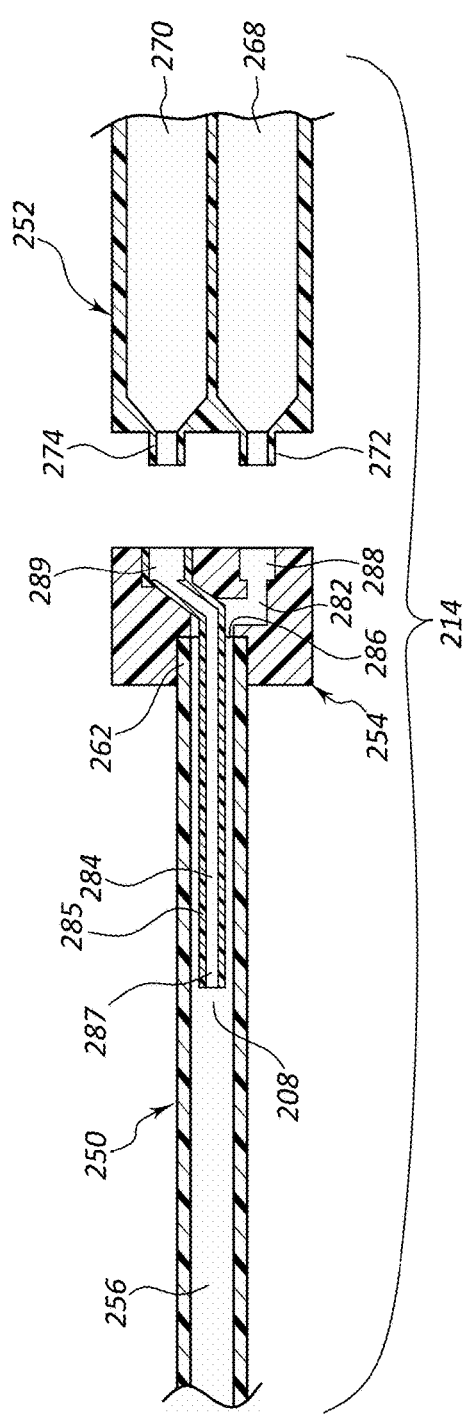
FIG. 3D is a partially exploded view of the balloon inflation device shown in FIG. 3C.
Figure 3E:
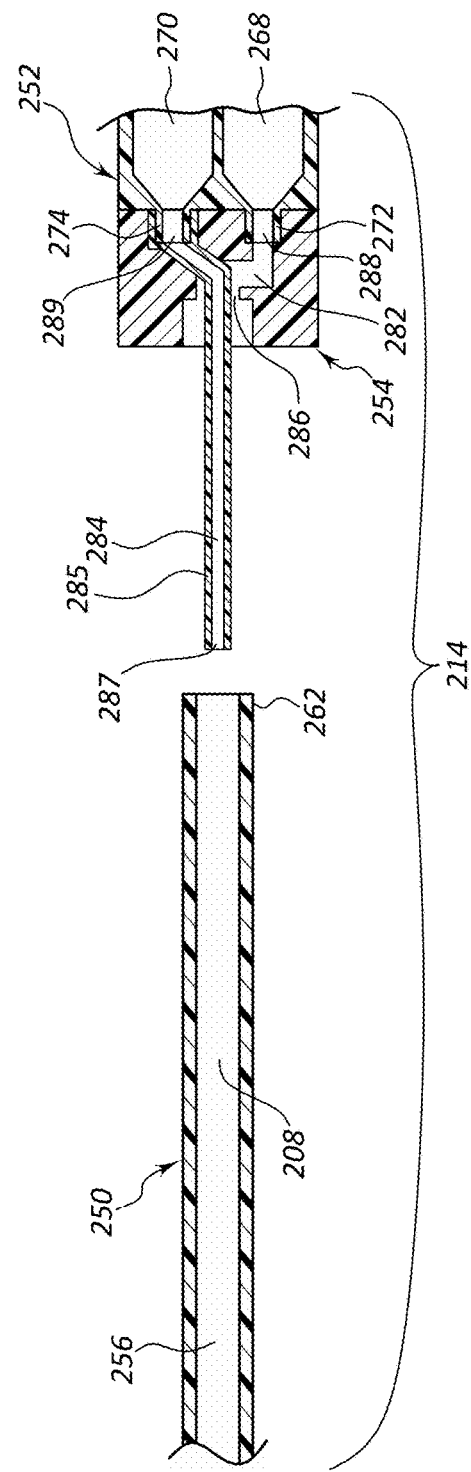
FIG. 3E is another partial exploded view of the balloon inflation device of FIG. 3C.

Referring now to FIGS. 3-3E, another example sealant delivery device 214 includes a delivery tube 250, a sealant container 252, and an adaptor 254. The delivery tube 250 includes a sealant lumen 256 and an exchange lumen 258 (see FIG. 3A). The sealant lumen 256 includes distal and proximal ends 260, 262. The exchange lumen 258 includes a side opening 266 and a distal opening 264.

The sealant container 252 includes first and second sealant chambers 268, 270, first and second delivery tips 272, 274, and a plunger 276. The plunger 276 includes first and second plunger member 278, 280 and an actuator 279.

The adaptor 254 includes first and second sealant channels 282, 284. The first sealant channel 282 includes a first distal end 286 and a first port 288. The second sealant channel 284 includes a second distal end 287 and a second port 289. The second sealant channel 284 may be defined by a tube 285 that extends within the sealant lumen 256. The tube 285 may be part of the adaptor 254 and extends distally therefrom. Alternatively, the tube 285 may be part of and mounted to the delivery tube 250. The second sealant channel 284 is connected in fluid communication with the second sealant chamber 270 via the second delivery tip 274 and the second port 289. The second sealant channel 284 terminates at a distal end of the tube 285 within the sealant lumen 256. The mixing area or zone 208 is positioned within the sealant lumen 256 adjacent to the second distal end 287. The mixing area 208 is spaced distally of the first and second delivery tips 272, 274, and may be positioned distal of the adaptor 254 and the proximal end 262 of the delivery tube 250.

In any of the sealant delivery device embodiments described above, the first and second sealant channels of the adaptor may be integrally formed with other portions of the adaptor as a single, unitary structure. The adaptor may be formed as a separate piece that is assembled with the delivery tube and sealant container in a separate assembly step during, for example, manufacturing or as part of preparing the sealant delivery device for use in treating a patient by an operator. FIGS. 3D and 3E show the sealant delivery device 214 dissembled in various arrangements.

FIG. 3D shows the sealant container 252 disconnected from the adaptor 254 and the adaptor 254 is mounted to the delivery tube 250. In one example, the adaptor 254 is permanently mounted to the delivery tube 250. The arrangement of FIG. 3D shows that the sealant container 252 may be used with different delivery tubes and adaptors and may be used with different procedures to advance a volume of the sealant components held therein into a delivery tube for mixing and ejection at a vessel puncture.

FIG. 3E shows the sealant delivery device 214 dissembled in a different arrangement wherein the sealant container 252 and adaptor 254 are connected together and disconnected from the delivery tube 250. The sealant container 252 and adaptor 254 may be permanently connected together. The combination of the sealant container 252 and adaptor 254 may be separated from the delivery tube 250 and used for sealing multiple different vessel punctures or used with multiple different delivery tubes or other structures for delivering a volume of sealing material to a single tissue puncture. In at least one example, the second distal end 287 of the tube 285 may be at least partially clogged with a mixture of first and second sealant components that have been mixed within sealant lumen 256 when the sealant delivery device 214 is assembled together as shown in FIG. 3C. The adaptor 254 may be removed from the delivery tube 250 and the second distal end 287 removed (e.g. cut off) so that the clogged portion does not inhibit flow of the second sealant component through the second sealant channel 284, thereby providing multiple uses of the sealant container 252 and adaptor 254.

Figure 4:
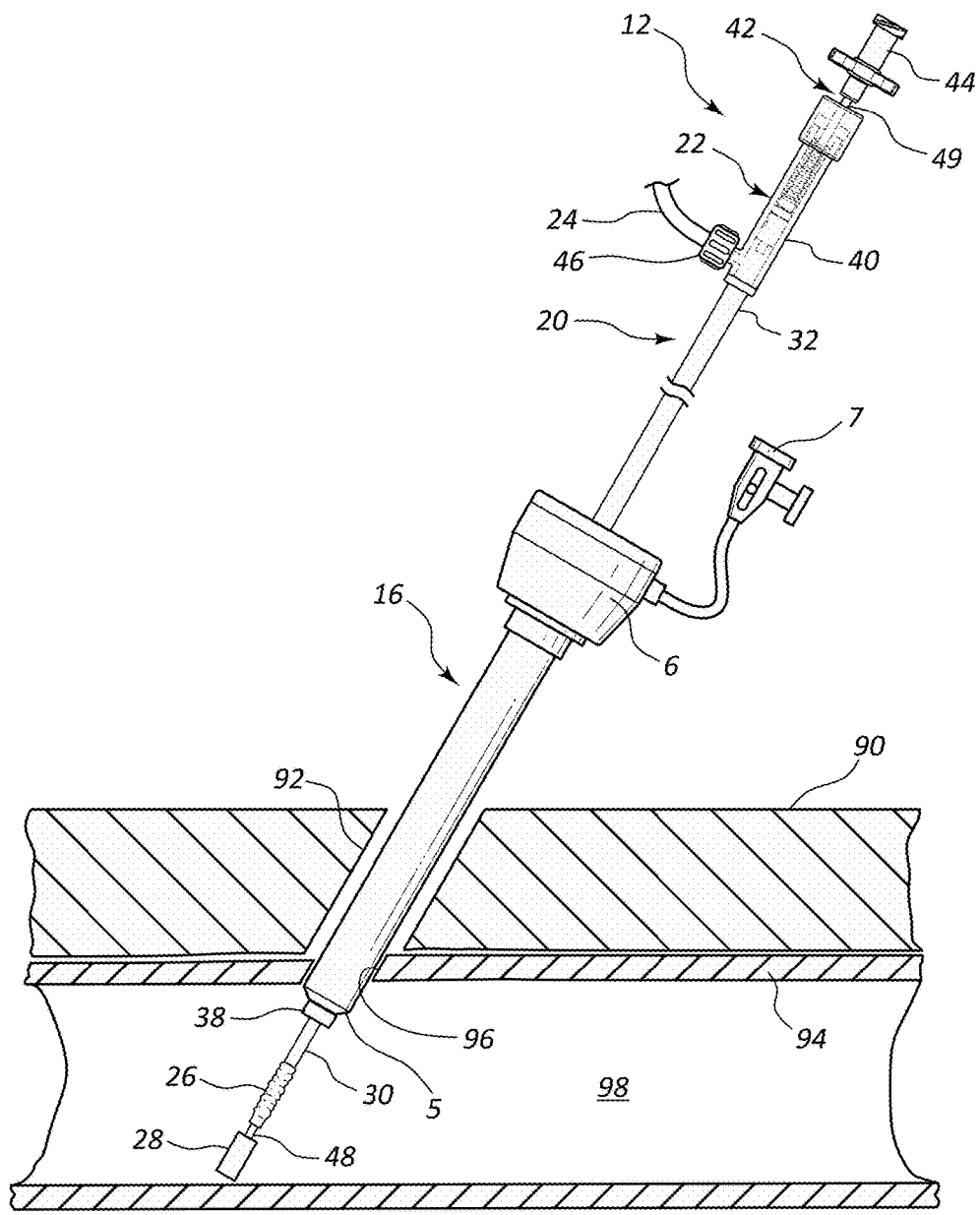
FIGS. 4-8 show steps of sealing a vascular closure using the vascular closure system of FIG. 1.

Referring now to FIGS. 4-8, an example method of sealing a vessel puncture is shown using the vascular closure system 10 of FIG. 1. FIG. 4 shows the sheath 16 inserted through a tissue tract 92 of a tissue layer 90 and a tissue puncture 96 of a vessel 94 into a vessel lumen 98. A distal end 5 of sheath 16 may be positioned within the vessel lumen 98. A hub 6 and ejection port 7 of the sheath 16 may be positioned outside of the patient. The balloon inflation device 12 is inserted through the sheath 16 until the balloon 26 and detachable tip 28 are positioned within the vessel lumen 98.

Figure 5:
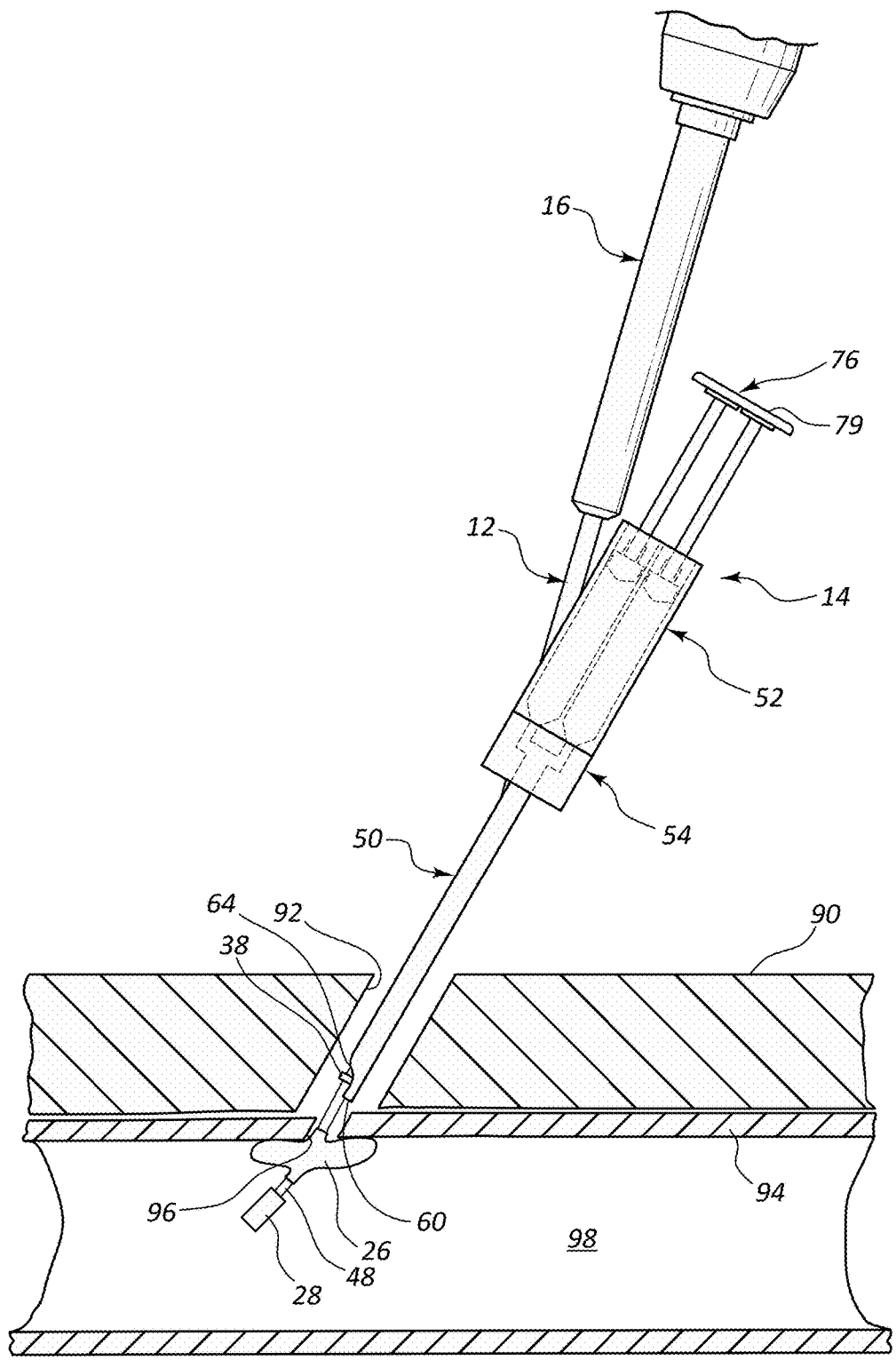
Figure 6:
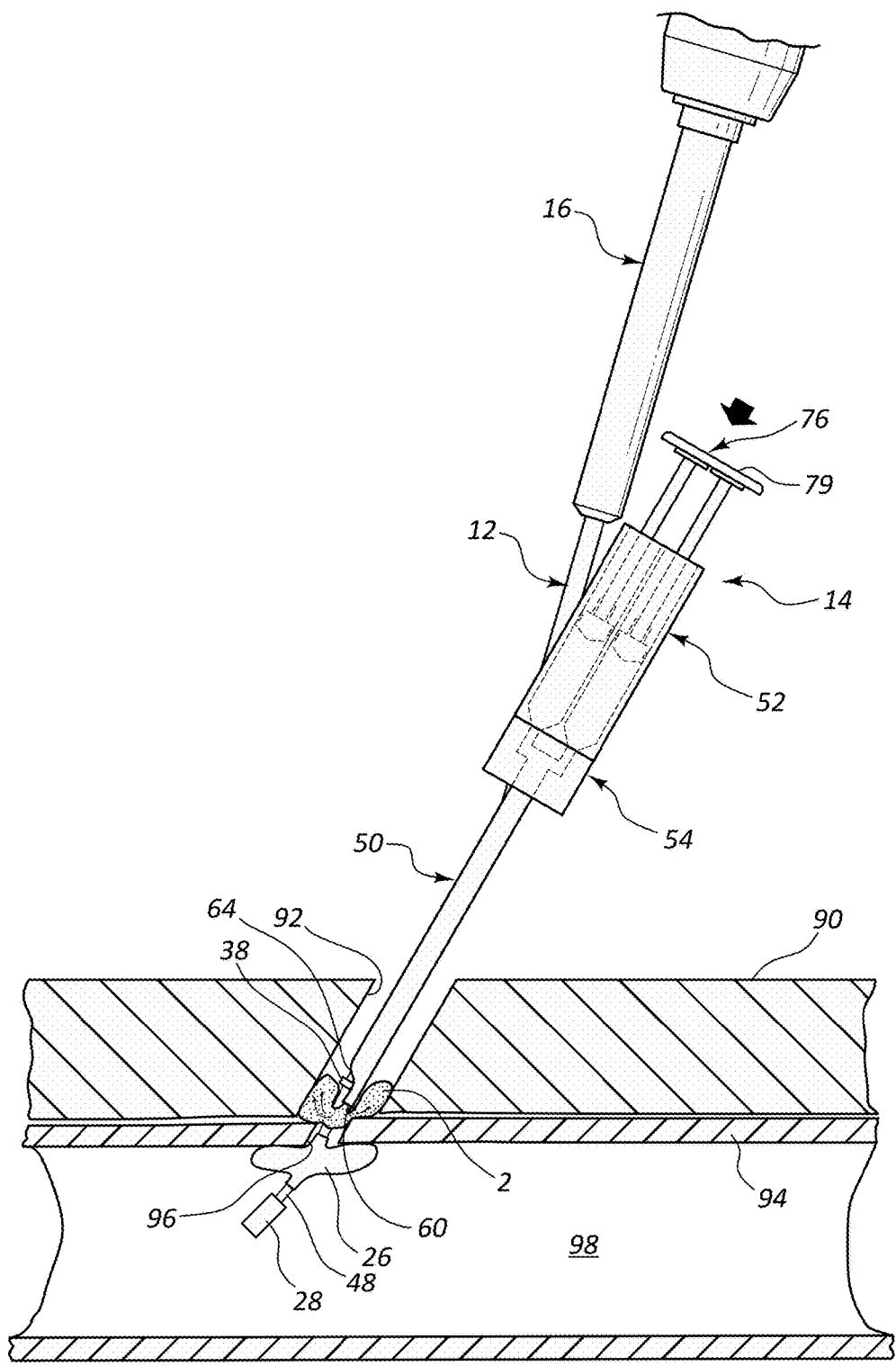

The balloon 26 is inflated by delivering a volume of inflation fluid from the inflation source 24 through the inflation port 46 to balloon 26. The inflated balloon 26 is withdrawn until it contacts an inner surface of the vessel 94 adjacent to the vessel puncture 96 to temporarily seal the vessel puncture 96 as shown in FIG. 5. The sheath 16 is withdrawn to provide easier, unobstructed access to the tissue tract 92 and vessel puncture 96 for delivering a sealant using the sealant delivery device 14. The sealant delivery device 14 may be connected to the balloon inflation device 12 at the exchange port 36 where the inflation tube 20 is inserted into the exchange lumen 58 of the delivery tube 50. The sealant delivery device 14 is advanced along the inflation tube 20 until contacting the collar 38. The collar 38 may be positioned along the inflation tube 20 at a predetermined distance from the balloon 26 that positions the distal end 60 of delivery tube 50 at a desired distance from the vessel puncture 96. Spacing the distal end 60 from the vessel puncture 96 may provide improve flow of the sealant into the vessel puncture 96 and tissue tract 92 as shown in FIG. 6. Some embodiments may be configured without the collar 38, which may make it easier to adjust a position of the sealant delivery device 14 relative to the balloon inflation device 12.

Figure 7:
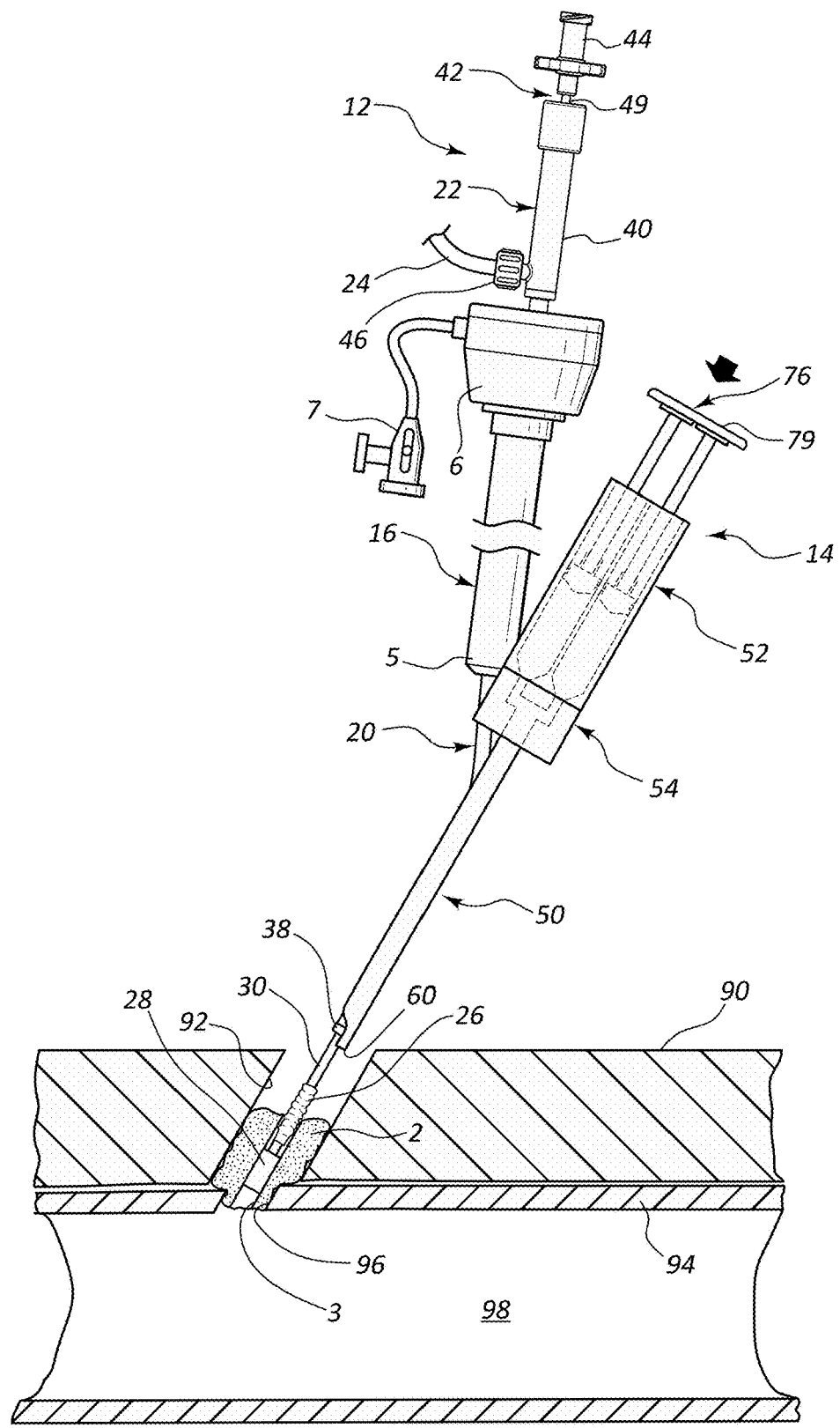

Referring to FIG. 6, the operator advances the plunger 76 to advance the first and second sealant components into the sealant lumen 56 where the sealant components are mixed and then ejected at distal end 60 into vessel puncture 96. The sealant material ejected into the vessel puncture 96 and tissue tract 92 cure or set to form a primary sealant plug 2 as shown in FIG. 7. The balloon 26 is deflated and the balloon inflation device 12 is withdrawn to remove the balloon 26 from the vessel puncture 96. The detachable tip 28 may be positioned within a plug channel 3 defined in the primary sealant plug 2 upon removal of the balloon 26. The detachable tip 28 may be detached within the plug channel 3 to further seal the vessel puncture 96.

Figure 8:
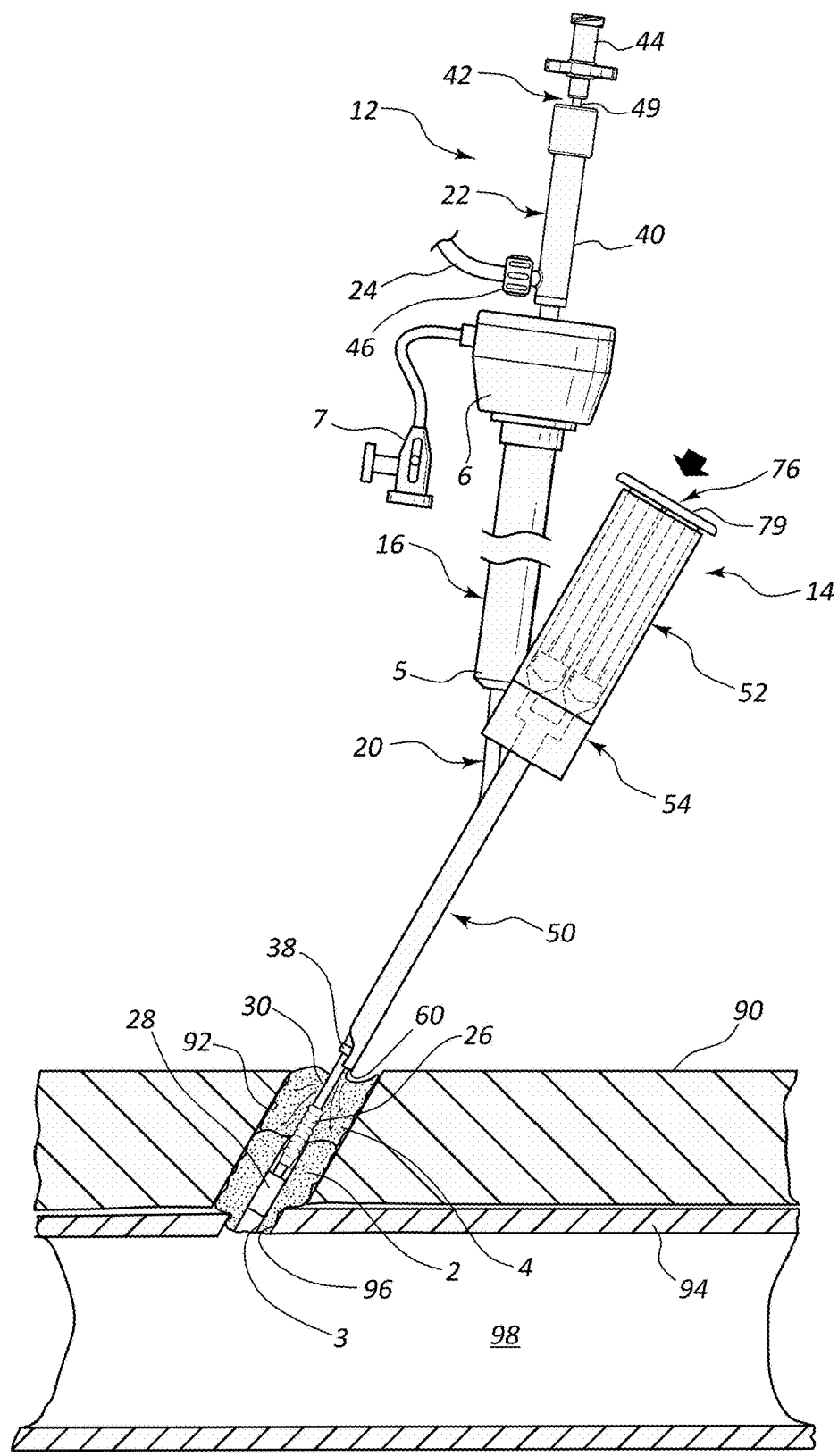

The sealant delivery device 14 may be positioned relative to the tissue tract 92 so that an additional flow of sealant material may be elected by the sealant delivery device 14 into the tissue tract 92. FIG. 8 shows the plunger 76 being operated further to advance more of the sealant material into tissue tract 92 to form a secondary sealant plug 4. The internal arrangement of sealant channels and lumens within the sealant delivery device 14 may make it possible to deliver the secondary flow of sealant material without clogging the outlet ports of the sealant container 52 or other flow paths of the sealant delivery device 14 that would otherwise prevent delivery of the secondary flow of sealant material in the secondary step that follows formation of the primary sealant plug 2.

In some arrangements, the sealant delivery device 14 may be maintained within the tissue tract 92 while the balloon inflation device 12 is completely removed from the tissue tract 92. Removing the balloon inflation device 12 from the tissue tract 92 may eliminate obstructions for the secondary flow of sealant material from the sealant delivery device 14 into the tissue tract 92.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A bioadhesive delivery system, comprising:
   a delivery tube having proximal and distal ends and a delivery lumen having proximal and distal ends, wherein the delivery lumen has a straight, elongated configuration and the distal end of the delivery lumen extends to the distal end of the delivery tube;
   wherein the delivery tube further comprises an exchange lumen having a proximal end and a distal end, wherein the distal end of the exchange lumen terminates proximal the distal end of the delivery tube;
   a bioadhesive container containing first and second chambers holding first and second sealant components, respectively;
   a plunger configured to contact an inner surface of the bioadhesive container and to advance through the first and second chambers;
   a channel arrangement having a first channel member providing flow communication between the first chamber and the delivery lumen, and a second channel member providing flow communication between the second chamber and the delivery lumen distal of the proximal end, the first and second channel members having laterally offset longitudinal axes relative to a longitudinal axis of the delivery lumen, at least one of the first or second channel members being connected in flow communication with the delivery lumen at an open proximal end of the delivery tube, the first channel member having a first cross-sectional shape, the second channel member having a second cross-sectional shape, the second cross-sectional shape being different from the first cross-sectional shape;
   wherein the channel arrangement is configured to isolate the first and second sealant components from each other until the first and second sealant components are positioned within the delivery tube;
   wherein the bioadhesive container is detachable from the delivery tube.

2. The bioadhesive delivery system of claim 1, wherein the second channel member is connected in flow communication with the delivery lumen through a side wall of the delivery tube.

3. The bioadhesive delivery system of claim 2, wherein the second channel member extends into the delivery lumen at an open proximal end of the delivery tube.

4. The bioadhesive delivery system of claim 2, wherein at least one of the first and second channel members comprises a length of tube.

5. The bioadhesive delivery system of claim 2, wherein at least a portion of the channel arrangement is permanently mounted to the delivery tube.

6. The bioadhesive delivery system of claim 2, wherein the channel arrangement is interposed between the bioadhesive container and the delivery tube.

7. The bioadhesive delivery system of claim 2, wherein the first sealant component comprises a precursor mixture and the second sealant component comprises an activator.

8. A sealant delivery device, comprising:
- a delivery tube having an open proximal end and a distal end, wherein the delivery tube has a straight, elongated configuration;
- wherein the delivery tube comprises a delivery lumen and an exchange lumen, each having proximal and distal ends, wherein the distal end of the exchange lumen is proximal the distal end of the delivery lumen;
- a bioadhesive container holding a sealant activator and a sealant precursor separated from each other;
- a plunger configured to contact an inner surface of the bioadhesive container and to advance the sealant activator and the sealant precursor into the delivery tube;
- an adapter interposed between the delivery tube and the bioadhesive container, the adapter having a first channel member that couples the delivery tube to the sealant activator, and a second channel member that couples the delivery tube to the sealant precursor, at least one of the first and second channel members opening into the open proximal end of the delivery tube, the first and second channel members each having cross-sectional shapes that are different from each other, the cross-sectional shapes of the first and second channel members being symmetrical across a centerline of the delivery tube, the first and second channel members having laterally offset parallel longitudinal axes along the delivery tube, the adapter providing separation of the sealant activator and the sealant precursor until the sealant activator and sealant precursor reach the delivery tube at a position distal of a proximal end of the delivery tube.

9. The sealant delivery device of claim 8, wherein the adapter includes a tube defining the second channel member and extending distal of a proximal end of the delivery tube.

10. The sealant delivery device of claim 8, wherein the delivery tube includes a first lumen and a second lumen arranged in parallel, the first and second lumens being connected in flow communication with the first and second channel members, respectively, the first and second lumens intersecting at the position distal of the proximal end of the delivery tube.

11. The sealant delivery device of claim 8, wherein the delivery tube is detachable from the bioadhesive container to replace the delivery tube and provide multiple uses for the bioadhesive container.

12. The sealant delivery device of claim 8, wherein the sealant precursor comprises a precursor mixture and the sealant activator comprises an activator.

13. A sealant delivery device, comprising:
- a delivery tube having an open proximal end and a distal end, wherein the delivery tube has a straight, elongated configuration;
- wherein the delivery tube comprises a delivery lumen and an exchange lumen, each having proximal and distal ends, wherein the distal end of the exchange lumen is proximal the distal end of the delivery lumen;
- a bioadhesive container holding a sealant activator and a sealant precursor separated from each other;
- a plunger configured to contact an inner surface of the bioadhesive container and to advance the sealant activator and the sealant precursor into the delivery tube;
- an adapter interposed between the delivery tube and the bioadhesive container, the adapter having a first channel member that couples the delivery tube to the sealant activator, and a second channel member that couples the delivery tube to the sealant precursor, at least one of the first and second channel members opening into the open proximal end of the delivery tube, the first and second channel members each having cross-sectional shapes that are different from each other, the first and second channel members having laterally offset parallel longitudinal axes along the delivery tube, the second channel member being positioned at least partially laterally external to the delivery lumen, the adapter providing separation of the sealant activator and the sealant precursor until the sealant activator and sealant precursor reach the delivery tube at a position distal of a proximal end of the delivery tube.

* * * * *